(12) United States Patent
Niddam-Hildesheim et al.

(10) Patent No.: US 7,396,839 B2
(45) Date of Patent: Jul. 8, 2008

(54) CRYSTALLINE FORMS OF GATIFLOXACIN

(75) Inventors: Valerie Niddam-Hildesheim, Ein Vered (IL); Shlomit Wizel, Petah Tiqva (IL); Greta Sterimbaum, Rishon-Lezion (IL)

(73) Assignee: Teva Pharmaceuticals USA, Inc., North Wales, PA (US)

( * ) Notice: Subject to any disclaimer, the term of this patent is extended or adjusted under 35 U.S.C. 154(b) by 128 days.

(21) Appl. No.: 10/635,337

(22) Filed: Aug. 6, 2003

(65) Prior Publication Data

US 2004/0192700 A1    Sep. 30, 2004

Related U.S. Application Data

(60) Provisional application No. 60/402,749, filed on Aug. 12, 2002, provisional application No. 60/401,672, filed on Aug. 6, 2002.

(51) Int. Cl.
*C07D 401/04*    (2006.01)
(52) U.S. Cl. .......................... 514/312; 546/156
(58) Field of Classification Search .................. 514/247, 514/312; 544/349; 546/156
See application file for complete search history.

(56) References Cited

U.S. PATENT DOCUMENTS 5,880,283 A * 3/1999 Matsumoto et al. ......... 544/363

6,413,969 B1    7/2002  Raghavan et al.

FOREIGN PATENT DOCUMENTS

| EP | 0 629 621 A | 12/1994 |
| EP | 0 805 156 A | 11/1997 |
| WO | WO 02 22126 | 3/2002 |
| WO | WO 2003/086402 | 10/2004 |

OTHER PUBLICATIONS

John Haleblian et al., "Pharmaceutical Applications of Polymorphism," Journal of Pharmaceutical Sciences, vol. 58, No. 8, Aug. 1969, pp. 911-929.

John K. Haleblian, "Characterization of Habits and Crystalline Modification of Solids and Their Pharmaceutical Applications," Journal of Pharmaceutical Sciences, vol. 64, No. 8, Aug. 1975, pp. 1269-1288.

G. Michael Wall, "Pharmaceutical Applications of Drug Crystal Studies," Pharmaceutical Manufacturing, vol. 3, No. 2, Feb. 1986, pp. 33-42.

* cited by examiner

*Primary Examiner*—James O. Wilson
*Assistant Examiner*—Paul V. Ward
(74) *Attorney, Agent, or Firm*—Kenyon & Kenyon LLP

(57) ABSTRACT

Provided are novel crystalline forms of gatifloxacin, denominated forms L, M, P, Q, S, and T1, and methods for making them. Also provided are methods of transforming the novel crystalline forms of gatifloxacin of the present invention to other crystalline forms of gatifloxacin.

36 Claims, 6 Drawing Sheets

Annotated Sheet
Matsumoto et al. Figure 5

Annotated Sheet
Matsumoto et al. Figure 6

CRYSTALLINE FORMS OF GATIFLOXACIN

CROSS-REFERENCE TO RELATED APPLICATIONS

This application claims the benefit under 35 U.S.C. § 119 (e) of provisional application Ser. No. 60/401,672, filed Aug. 6, 2002 and provisional application Ser. No. 60/402,749, filed Aug. 12, 2002, both of which are incorporated herein by reference.

FIELD OF THE INVENTION

The present invent relates to novel polymorphs and pseudopolymorphs of (±) 1-cyclopropyl-6-fluoro-1,4-dihydro-8-methoxy-7-(3-methyl-1-piperazinyl)-4-oxo-3-quinolinecarboxylic acid, commonly known as gatifloxacin.

BACKGROUND OF THE INVENTION

Gatifloxacin, known as (±) 1-cyclopropyl-6-fluoro-1,4-dihydro-8-methoxy-7-(3-methyl-1-piperazinyl)-4-oxo-3-quinolinecarboxylic acid, has the following structure:

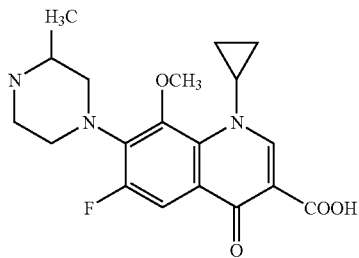

Gatifloxacin, an anti-bacterial agent, is marketed as Tequin® by Bristol-Myers Squibb. Tequin® is available in a dosage of 200 and 400 mg in the form of a vial or a tablet, which can be either injected or taken orally.

Many pharmaceutically active organic compounds can crystallize in more than one type of molecular packing with more than one type of internal crystal lattice. That is, the compounds crystallize in different crystalline forms. The respective resulting crystal structures (forms) can have, for example, different unit cells. This phenomenon—identical chemical structure but different internal structure—is referred to as polymorphism and the species having different molecular structures are referred to as polymorphs.

Many pharmacologically active organic compounds can also crystallize in crystalline forms such that second, foreign molecules, especially solvent molecules, are regularly incorporated into the crystal structure of the principal pharmacologically active compound. This phenomenon is sometimes referred to as pseudopolymorphism and the resulting structures as pseudopolymorphs. When the second molecule is a solvent molecule, the pseudopolymorphs can be referred to as solvates.

However, it is generally not possible to predict whether a particular organic compound will form different crystalline forms, let alone predict the structure and properties of the crystalline forms themselves.

The discovery of a new crystalline form of a pharmaceutically useful compound provides an opportunity to improve the performance characteristics of a pharmaceutical product. It enlarges the repertoire of materials that a formulation scientist has available for designing, for example, a pharmaceutical dosage form of a drug with a targeted release profile or other desired characteristic. It is clearly advantageous when this repertoire is enlarged by the discovery of new polymorphs or pseudopolymorphs of a useful compound. For a general review of polymorphs and the pharmaceutical applications of polymorphs see G. M. Wall, *Pharm Manuf.* 3, 33 (1986); J. K. Haleblian and W. McCrone, *J Pharm. Sci.*, 58, 911 (1969); and J. K. Haleblian, *J Pharm. Sci.*, 64, 1269 (1975), all of which are incorporated herein by reference.

Crystalline forms can be influenced by controlling the conditions under which the compound is obtained in solid form. Solid state physical properties that can differ from one polymorph to the next include, for example, the flowability of the milled solid. Various crystalline forms can be more or less hygroscopic. Absorption of atmospheric moisture by compound in powder form can impede its ability to flow. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound that can vary from one polymorph or pseudopolymorph to the next is its rate of dissolution in aqueous media, e.g., gastric fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation, orientation, and packing of molecules in the unit cell, which characterize a particular polymorphic or pseudopolymorphic form of a substance. A polymorphic form may have thermodynamic properties different from those of the amorphous material or another polymorphic form. Thermodynamic properties can be used to distinguish between various polymorphs or pseudopolymorphs. Thermodynamic properties that can be used to distinguish between polymorphs and pseudopolymorphs can be measured in the laboratory by such techniques as capillary melting point, thermogravimetric analysis (TGA), differential scanning calorimetry (DSC), and differential thermal analysis (DTA).

A particular crystalline form can also possess distinct spectroscopic properties that may be detectable by, for example, solid state $^{13}C$ NMR spectroscopy and infrared (IR) spectroscopy. This is particularly so in the case of crystalline forms that are solvates because of the presence of absorptions or resonances due to the second, foreign molecule.

(±)-1-Cyclopropyl-6-fluoro-1,4-digydro-8-methoxy-7-(3-methyl-1-piperazinyl)-4-oxo-3-quinolenecarboxylic acid, commonly known as gatifloxacin, is a synthetic broad-spectrum antibacterial agent for oral or intravenous administration.

U.S. Pat. No. 5,880,283 (the '283 patent) discloses that gatifloxacin forms a hygroscopic hemihydrate. The hemihydrate (a pseudopolymorph) is reported to be easily formed upon crystallization of gatifloxacin from water-containing organic solvents. The hemihydrate reportedly has disadvantages for manufacturing of solid oral dosage forms, e.g., tablets. The patent further discloses a novel pseudopolymorph of gatifloxacin, the sesquihydrate, and presents thermal analysis and x-ray diffraction data for this material. The sesquihydrate is reported to be less hygroscopic and more stable in manufacturing.

U.S. Pat. No. 6,413,969 discloses at least 12 different polymorphs or pseudopolymorphs of gatifloxacin and discloses the x-ray powder diffraction diagrams of at least 10 of these. The hexahydrate, pentahydrate and sesquihydrate are crystallized directly from aqueous solvents. Other crystalline forms are crystallized from a molten phase or by solid-solid phase transformations. The pentahydrate form is, according to the disclosure of U.S. Pat. No. 6,413,969, the most thermodynamically stable form and has the lowest aqueous solubility at room temperature. The interrelationships between the twelve identified crystalline forms are given in the application.

SUMMARY OF THE INVENTION

In one aspect, the present invention relates to a crystalline form of gatifloxacin, denominated form L, that is characterized by an x-ray reflection at about $17.2°\pm0.2°$ $2\theta$.

In another aspect, the present invention relates to a method of making gatifloxacin form L including the steps of: providing, at a temperature of at least about 70° C., a solution of gatifloxacin in a solvent consisting essentially of a mixture of methanol and water, wherein the volume percent water is about 5 vol-% to about 15 vol-%, especially about 10 vol-%; cooling the solution to ambient temperature and thereafter to a temperature of about 0° C. to about 10° C., especially about 5° C., to obtain a suspension; isolating the solid from the suspension; and drying the isolated solid at a temperature of about 40° C. to about 70° C., especially about 55° C., to obtain the crystalline form L of gatifloxacin.

In another aspect, the present invention relates to a crystalline form of gatifloxacin, denominated form M, characterized by x-ray reflections at about 8.8°, 14.1°, 17.6°, 18.2°, 22.0°, and $22.6°\pm0.2°$ $2\theta$.

In another aspect, the present invention relates to a method of making gatifloxacin form M including the steps of: slurrying gatifloxacin in ethanol, wherein the gatifloxacin slurried is selected from form T1RP, T1, and mixtures of these; isolating the solid from the slurry; and drying the isolated solid at ambient temperature and pressure to obtain the crystalline form of gatifloxacin.

In a further aspect, the present invention relates to a crystalline form of gatifloxacin, denominated from P, characterized by x-ray reflections at about 11.1°, 11.7°, 12.5° and $23.0°\pm0.2°$ $2\theta$.

In another aspect, the present invention relates to a method of making gatifloxacin form P including the steps of: providing, at a temperature of at least about 75° C., a solution of gatifloxacin in a solvent consisting essentially of a mixture of ethanol and water, wherein the volume percent ethanol in the mixture is at least about 95 vol-%, especially about 99 vol-%; cooling the solution to ambient temperature and thereafter to a temperature of about 0° C. to about 10° C., especially about 5° C., whereby a suspension is obtained; and isolating the crystalline form of gatifloxacin from the suspension.

In another embodiment, the present invention relates to a crystalline form of gatifloxacin, denominated form Q, characterized by x-ray reflections at about 6.8°, 7.1°, 11.1°, 15.5°, and $17.4°\pm0.2°$ $2\theta$.

In a further aspect, the present invention relates to a method of making gatifloxacin form Q including the steps of: providing, at reflux, a solution of gatifloxacin in a solvent consisting essentially of a mixture of acetonitrile and water, wherein the volume percent water in the mixture is about 2 vol-%; cooling the solution to ambient temperature and thereafter to a temperature of about 0° C. to about 10° C., especially about 5° C., whereby a suspension is obtained; isolating the solid from the suspension; and d) drying the isolated solid at about 50° C. and a pressure of about 10 to about 400 mm Hg to obtain the crystalline form of gatifloxacin.

In still a further aspect, the present invention relates to a novel crystalline form of gatifloxacin, denominated form T1, characterized by x-ray reflections at about 7.4°, 8.9°, 9.6°, 11.4°, 12.2°, 12.9°, 14.1°, 16.7°, 21.2°, 21.8°, 24.1°, and $26.0°\pm0.2°$ $2\theta$.

In yet another aspect, the present invention relates to a method of making gatifloxacin form T1 including the steps of crystallizing gatifloxacin from acetonitrile; isolating the gatifloxacin crystallized from acetonitrile; slurrying the gatifloxacin so isolated in ethanol for a slurry time of about 2 hours or less; and isolating gatifloxacin form T1.

In another aspect, the present invention relates to a novel crystalline form of gatifloxacin, denominated form S, characterized by x-ray reflections at about 9.3°, 11.0°, and $21.2°\pm0.2°$ $2\theta$. Form S can be further characterized by x-ray reflections at about 12.0°, 14.5°, and $18.6°\pm0.2°$ $2\theta$.

In yet another aspect, the present invention relates to a method of making gatifloxacin form S including the steps of: crystallizing gatifloxacin from acetonitrile; isolating the gatifloxacin crystallized from acetonitrile; slurrying the gatifloxacin so isolated in a lower alkanol having 1 to 4 carbon atoms for a slurry time of at least about 2 hours; and isolating the crystalline form S of gatifloxacin from the slurry.

In a further embodiment, the present invention relates to methods of making gatifloxacin hemihydrate, sesquihydrate, and form omega, which methods include the step of treating one or more of the novel crystalline forms of the present invention, for example by heating or aging.

DETAILED DESCRIPTION OF THE INVENTION

Figure 1:
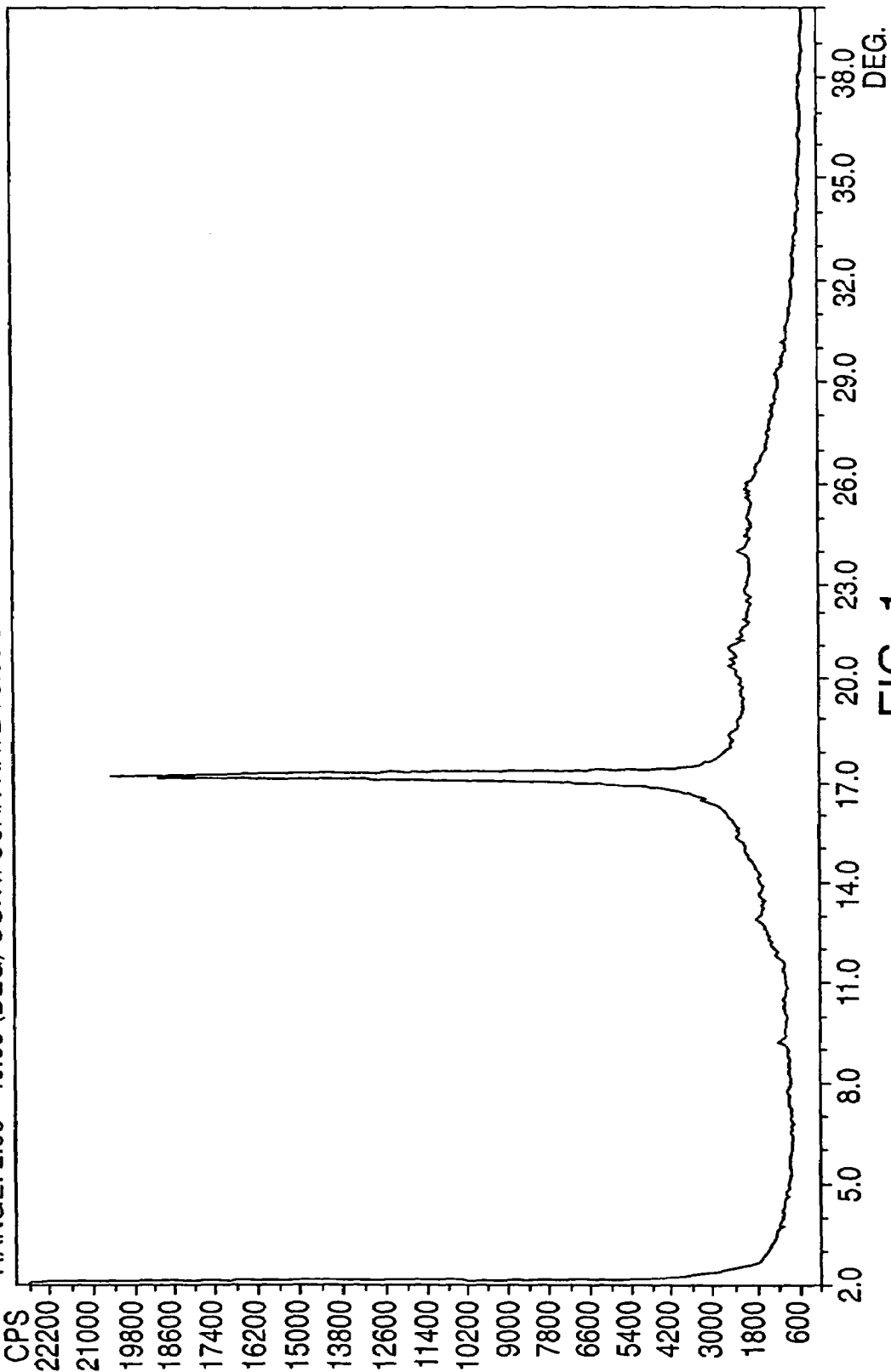
FIG. 1 is a representative x-ray diffraction diagram of gatifloxacin form L.

As used herein in connection with a measured quantity, the term about refers to that variation in the measured quantity as would be expected by the skilled artisan making the measurement and exercising a level of care commensurate with the objective of the measurement and the precision of the measuring equipment used.

As used herein in connection with the composition of a mixture of solvents, volume % (vol-%), % v:v, and N % v/v (where N is a number from 1 up to and including 100) are synonymous and calculated as follows (illustrated for species A):

$$\text{Vol-}\%_A = Wt_A \times \rho_A / (Wt_A \times \rho_A + Wt_B \times \rho_B)$$

where:

$Wt_A$ and $Wt_B$ are the weights in grams of species A and B, respectively, and $\rho_A$ and $92_B$ are the densities, in g./mL. of species A and B, respectively.

As used herein, the term "ambient temperature" refers to a temperature of about 20° C. to about 30° C.

As used herein, the term "ambient pressure" refers to a pressure of about 750 mm Hg to about 765 mm Hg.

As used herein in connection with drying of samples of gatifloxacin, the term "reduced pressure" means a pressure of about 1 to about 600 mm Hg.

As used herein, the term "form omega" ($\Omega$) refers to the crystalline form of gatifloxacin disclosed under that designation in Raghavan et al., U.S. Pat. No. 6,413,969 (the '969 patent).

As used herein, the term gatifloxacin "sesquihydrate" refers to the crystalline form of gatifloxacin disclosed under that designation in the '969 and '283 patents.

As used herein, the term "form T2RP" refers to the hemihydrate crystalline form of gatifloxacin disclosed under that designation in the '969 patent.

As used herein, the term "form J" refers to a crystalline form of gatifloxacin that can be characterized by x-ray reflections at about 67°, 11.3°, 13.8°, and 16.4°±0.2° 2θ. Form J can be obtained by methods described in the working examples, infra.

X-ray reflections reported herein were determined by x-ray diffraction. X-ray diffraction refers to x-ray diffraction by the powder diffraction technique. X-ray powder diffraction analysis was performed using a Scintag powder diffractometer with variable goniometer, a Cu $K^\alpha$ source, and a solid state detector. A standard round aluminum sample holder with zero background quartz plate was used. Samples were scanned from 2° to 40° 2θ at 3° per minute in the continuous scan mode. Reflections are reported as peak maxima in the intensity vs. 2θ plots obtained, and are subject to the normal experimental error (uncertainty), estimated at ±0.2°. Description of samples as "wet" indicates that samples were promptly analyzed "as is".

In particular embodiments, the novel crystalline forms of the present invention are made by a crystallization method, which can include a treatment step (e.g. a drying step), whereby the crystalline form, or penultimate precursor thereof, is caused to precipitate from a provided solution, whereby a suspension (slurry) is obtained. In certain embodiments employing a crystallization method, precipitation is effected by reducing the temperature of a provided solution of the compound in a solvent of fixed composition. Depending on the crystalline form desired, it may be necessary to regulate the rate at which the temperature of the solution is reduced (i.e. the cooling rate).

In other embodiments employing a crystallization method, precipitation is effected by altering the composition of the solvent of the provided solution, for example by adding an antisolvent to the provided solution, so that, at a given temperature, the solubility of the compound in the solvent of altered composition is less than the solubility of the compound in the original solvent of the provided solution. Alteration of the composition of the solvent of the provided solution (e.g. by addition of antisolvent) can be accompanied or followed by reduction of the temperature of the resulting solution.

An antisolvent is an organic compound, normally a liquid at ambient temperature, that is a poor solvent for the compound to be crystallized (here gatifloxacin). The solubility of the compound to be crystallized in the combination of solvent of the provided solution and anti-solvent is lower than the solubility of the compound in the solvent of the solution originally provided.

Any embodiment of a crystallization method can include the well-known step of seeding, whereby crystals of the compound to be crystallized, or a foreign material, are added to the solution at a seeding temperature selected such that the seed crystals remain substantially undissolved.

In other embodiments, the novel crystalline forms of the present invention can be made by a slurry (suspension) method including the step of combining, with agitation, gatifloxacin with a slurry solvent, in which gatifloxacin is sparingly soluble, for a slurry time. The desired crystalline form is either isolated form the slurry, or obtained by treating (e.g. drying) the solid isolated from the slurry at the end of the slurry time.

Unless otherwise noted, the relative proportions of solid and slurry solvent are not critical. The combining can be in any suitable vessel equipped with an agitator capable of dispersing the solid in the slurry solvent and providing for intimate mixing of the solid and slurry solvent. The slurry process is carried-out for a time ("slurry time") sufficient to substantially complete the formation of the desired crystalline form. The skilled artisan will know to adjust the slurry time through routine optimization by, for example, monitoring the crystalline form of the solid in the slurry using any method (e.g. x-ray diffraction) by which the desired crystalline form can be characterized. Slurry times disclosed herein are approximate and based on experience. Longer slurry times may be required depending on, for example, temperature, the relative proportions of solid and slurry solvent, and the equipment used. Shorter times can also be sufficient.

In either a crystallization or slurry method, a suspension (slurry) of solid and liquid is obtained. The solid can be isolated from the suspension by any means known in the art, for example filtration (gravity or suction) or centrifugation, to mention just two.

In another embodiment, the present invention provides a novel crystalline form of gatifloxacin, denominated form L, that can be characterized by a reflection in x-ray diffraction at about 17.2°±0.2°2θ. A representative x-ray diffraction diagram of Form L is shown in FIG. 1.

The novel crystalline form described in the immediately preceding paragraph can be made by a crystallization method including the steps of providing, at a temperature of at least about 70° C., preferably at reflux, a solution of gatifloxacin in a mixture of methanol and water having between about 5 vol-% and about 15 vol-% water (i.e. 95:5 to 85:15, v:v, methanol/water), preferably about 10 vol-% water; cooling the solution to ambient temperature and thereafter to a temperature of about 0° C. to about 10° C. to obtain a suspension; isolating the solid from the suspension; and drying the isolated solid at about 40° C. to about 70° C. to obtain the novel crystalline form of gatifloxacin.

Upon prolonged (e.g. 2 months) storage at ambient temperature and pressure, form L converts to form $\Omega$.

Figure 2:
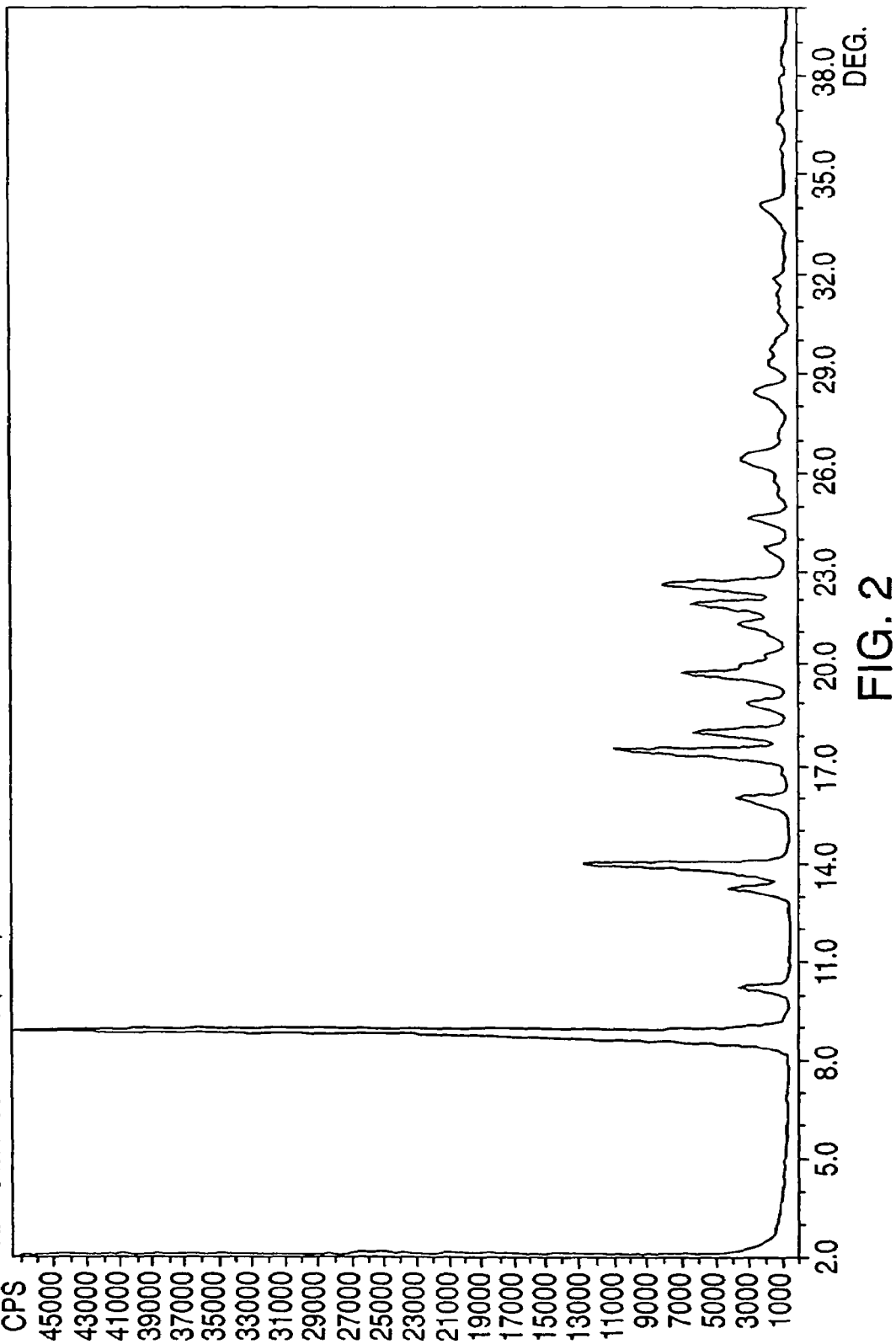
FIG. 2 is a representative x-ray diffraction diagram of gatifloxacin form M.

In another embodiment, the present invention provides a novel crystalline form of gatifloxacin, denominated form M, characterized by reflections in x-ray diffraction at about 8.8°, 14.1°, 17.6°, 18.2°, 22.0°, and 22.6°±0.2° 2θ. A representative x-ray diffraction diagram of form M is shown in FIG. 2.

The novel crystalline form of gatifloxacin described in the immediately preceding paragraph can be made by a slurry process including the step of slurrying gatifloxacin selected from form T1, T1RP, and mixtures of these in absolute ethanol (EtOH) for a slurry time, isolating the solid from the slurry, and drying the isolated solid at about 50° C. at reduced pressure to obtain the novel crystalline form of gatifloxacin.

Upon prolonged (e.g. 2 months) storage at ambient temperature and pressure, form M converts to form T2RP (hemihydrate).

Figure 3:
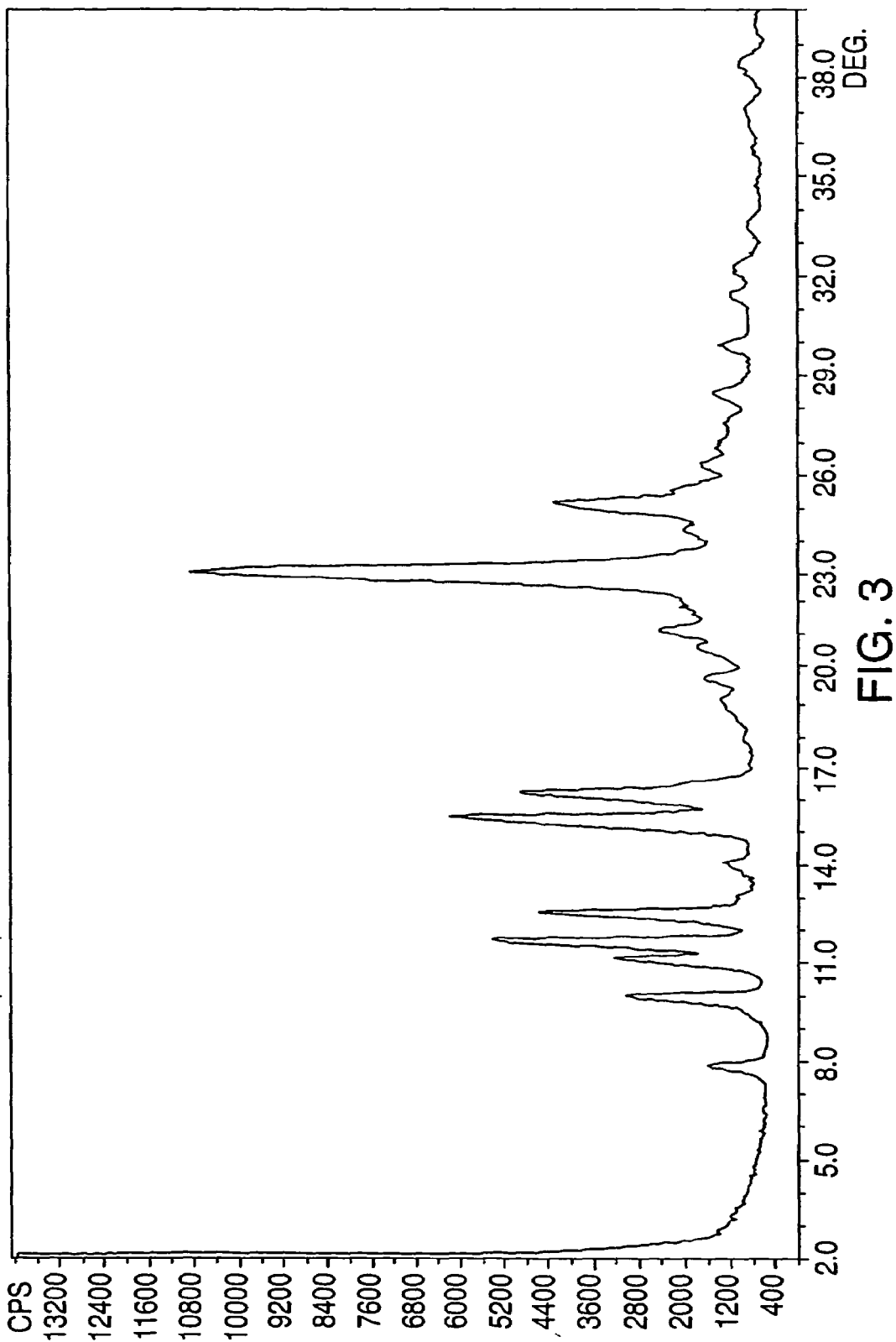
FIG. 3 is a representative x-ray diffraction diagram of gatifloxacin form P.

In another embodiment, the present invention provides a novel crystalline form of gatifloxacin, denominated form P, characterized by x-ray reflections at about, 11.1°, 11.7°, 12.5°, and 23.0°±0.2° 2θ. A representative x-ray diffraction diagram of form P is shown in FIG. 3.

The novel crystalline form of gatifloxacin described in the immediately preceding paragraph can be made by a crystallization process including the steps of providing, at a temperature of at least about 75° C., preferably at reflux, a solution of gatifloxacin in a mixture of ethanol and water having at least about 95 vol-% ethanol; cooling the solution to ambient temperature and thereafter to a temperature of about 0° C. to about 10° C., to obtain a suspension; and isolating the novel crystalline form of gatifloxacin from the suspension.

Upon prolonged (e.g. 1 month) storage at ambient temperature and pressure, form P converts to gatifloxacin sesquihydrate. Heating form P at about 50° C. results in gatifloxacin form T1, infra.

Figure 4:
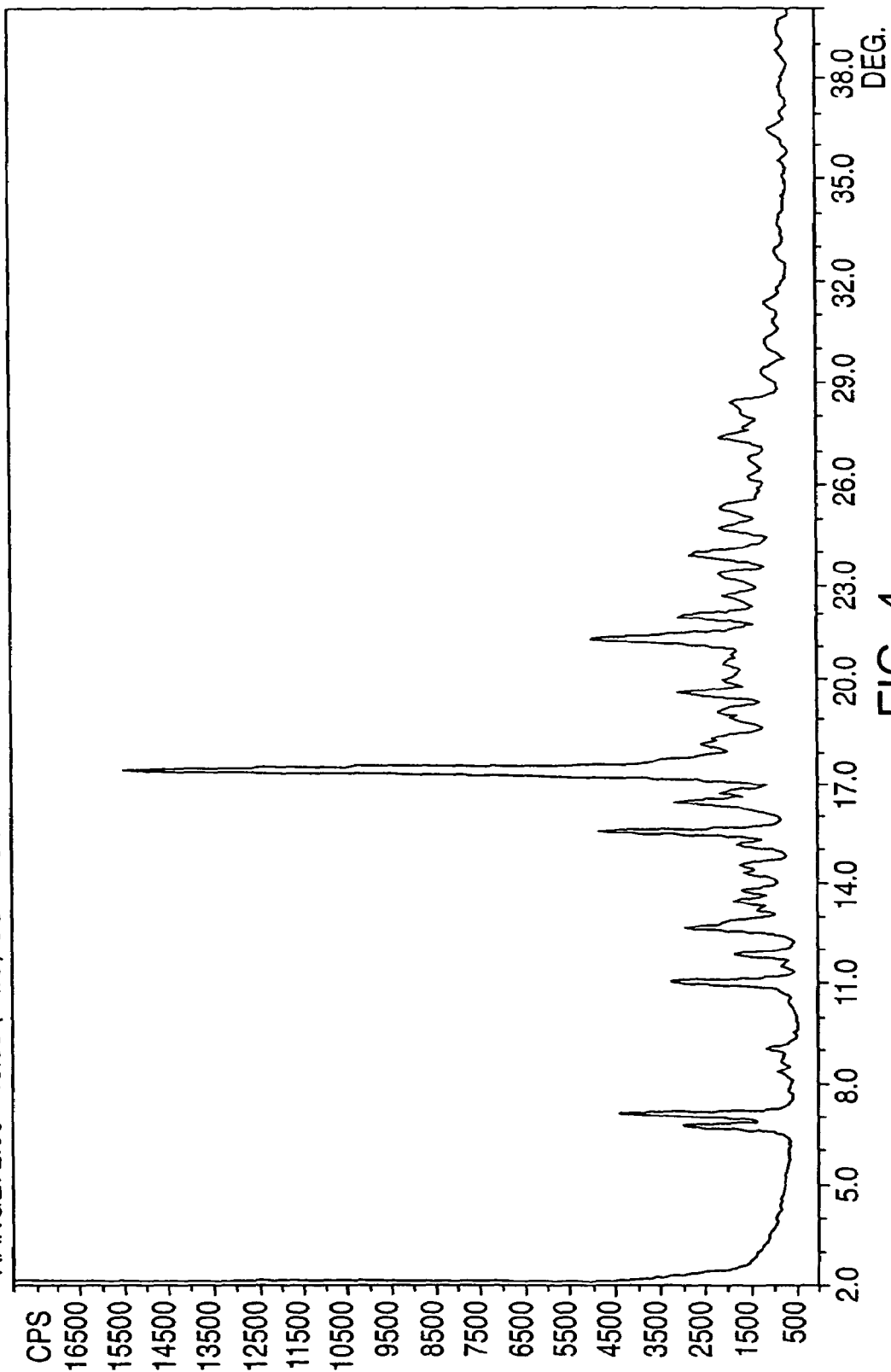
FIG. 4 is a representative x-ray diffraction diagram of gatifloxacin form Q.

In yet a further embodiment, the present invention provides a novel crystalline form of gatifloxacin, denominated form Q, characterized by reflection in x-ray diffraction at about 6.8°, 7.1°, 11.1°, 15.5°, and 17.4°±0.2° 2θ. A representative x-ray diffraction diagram of form Q is shown in FIG. 4.

The novel crystalline form of gatifloxacin described in the immediately preceding paragraph can be made by a crystallization method including the steps of providing, at a temperature of at least about 75° C., preferably at reflux, a solution of gatifloxacin and acetonitrile (ACN) having about 2 vol-% water (i.e. ACN/H$_2$O 98:2 v:v); cooling the solution to ambient temperature and thereafter to a temperature of about 0° C. to about 10° C. to obtain a suspension; isolating the solid from the suspension; and drying the isolated solid at about 50° C. and reduced pressure, to obtain the novel crystalline form of gatifloxacin.

Figure 5:
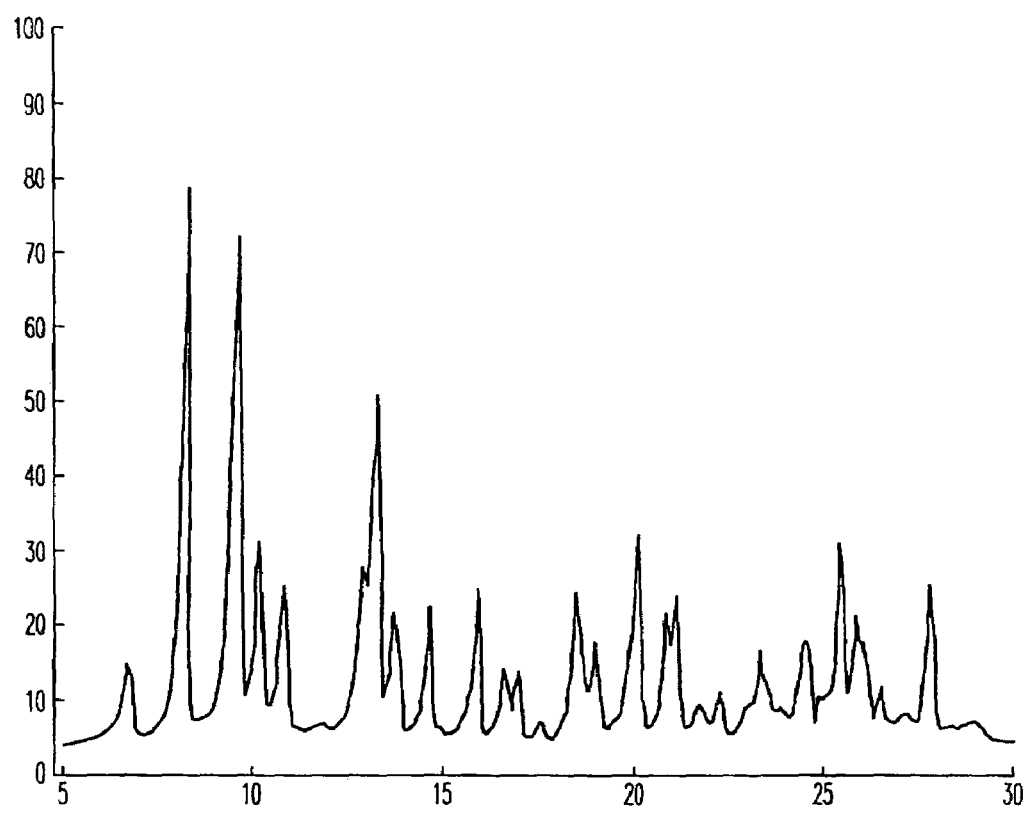
FIG. 5 is a representative x-ray diffraction diagram of gatifloxacin form S.

In still a further embodiment, the present invention provides a method of making a novel crystalline form of gatifloxacin, denominated form S, characterized by reflections in x-ray diffraction at about 9.3°, 11.0°, and 21.2°±0.2° 2θ and additional x-ray reflections at about 12.0°, 14.5°, and 18.6°±0.2° 2θ. A representative x-ray diffraction diagram of form S is shown in FIG. 5.

The novel crystalline form of gatifloxacin described in the immediately preceding paragraph can be made by a slurry method including the steps of crystallizing gatifloxacin from acetonitrile, isolating the gatifloxacin crystallized from acetonitrile; slurrying the gatifloxacin so isolated in a lower alkanol having from 1 to 4, preferably 2, carbon atoms for a time of at least about 2 hours; and isolating the crystalline form of gatifloxacin.

Figure 6:
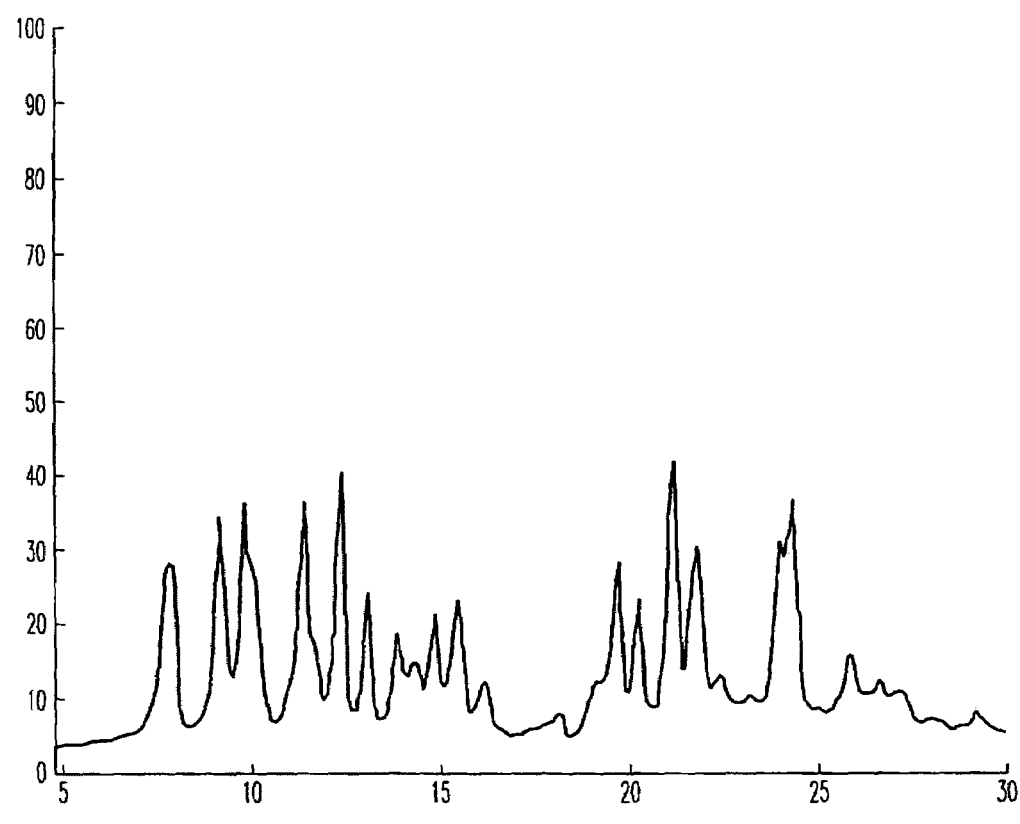
FIG. 6 is a representative x-ray diffraction diagram of gatifloxacin form T1.

In another embodiment, the present invention provides a novel crystalline form of gatifloxacin, denominated form T1, characterized by reflections in x-ray diffraction at about 7.4°, 8.9°, 9.6°, 11.4°, 12.2°, 12.9°, 14.1°, 21.2°, 21.8°, 24.1°, and 26.0°±0.2° 2θ. A representative x-ray diffraction diagram of form T1 is shown in FIG. 6.

The novel crystalline form of gatifloxacin described in the immediately preceding paragraph can be made by a process including the steps of: crystallizing gatifloxacin from acetonitrile; isolating the gatifloxacin crystallized from acetonitrile; slurrying the gatifloxacin so isolated in a lower alkanol having from 1 to 4, preferably 2, carbon atoms for a time of about 2 hours or less, preferably less; and isolating the crystalline form of gatifloxacin.

In still yet a further embodiment, any of the novel crystalline forms of gatifloxacin, forms L, M, P, Q, S and T1 described hereinabove, alone or in any combination, are formulated into a pharmaceutical composition, preferably an oral solid dosage form or a dosage form for parental administration.

The pharmaceutical composition can be in the form of a solid oral dosage form (e.g., compressed tablets or capsules), or it can be in the form of a liquid oral dosage form (e.g., a solution or oral suspension). It was found that E1 is also stable in formulations at 30° C. for at least 3 months.

Compressed tablets can be made by dry or wet granulation methods as is known in the art. In addition to the pharmaceutically active agent or drug, compressed tablets contain a number of pharmacologically inert ingredients, referred to as excipients. Some excipients allow or facilitate the processing of the drug into tablet dosage forms. Other excipients contribute to proper delivery of the drug by, for example, facilitating disintegration.

Excipients can be broadly classified according to their intended function. This classification is sometimes arbitrary and it is known that a particular excipient can function in more than one way or serve more than one purpose in a formulation.

Diluents increase the bulk of a solid pharmaceutical composition and may make a pharmaceutical dosage form containing the composition easier for the patient and caregiver to handle. Diluents for solid compositions include, for example, microcrystalline cellulose (e.g., AVICEL®, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate and starch. The dissolution rate of a compacted solid pharmaceutical composition in the patient's stomach may be increased by the addition of a disintegrant to the composition.

Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®) and starch.

Glidants can be added to improve the flow properties of non-compacted solid compositions and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Solid and liquid compositions may also be colored using any pharmaceutically acceptable colorant to improve their appearance and/or facilitate patient identification of the product and unit dosage level.

Of course, wet or dry granulate can also be used to fill capsules, for example gelatin capsules. The excipients chosen for granulation when a capsule is the intended dosage form may or may not be the same as those used when a compressed tablet dosage form is contemplated.

Selection of excipients and the amounts to use may be readily determined by the formulation scientist based upon experience and consideration of standard procedures and reference works in the field.

In liquid pharmaceutical compositions of the present invention, one of gatifloxacin forms L, M, P, Q, S, and T1, or mixtures thereof, and any other solid excipients are dissolved or suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity enhancing agent to improve the mouth-feel of the product and/or coat the lining of the gastrointestinal tract. Such agents include, for example, acacia, alginic acid, bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as gluconic acid, lactic acid, citric acid or acetic acid, sodium gluconate, sodium lactate, sodium citrate or sodium acetate.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. The most suitable route in any given case will depend on the nature and severity of the condition being treated. The dosages can be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs.

The active ingredient and excipients can be formulated into compositions and dosage forms according to methods known in the art.

A composition for tableting or capsule filling can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the active ingredients and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

Capsules, tablets and lozenges and other unit dosage forms may be administered in various dosages depending on the need.

The present invention is illustrated in certain of its embodiments by the following nonlimiting examples.

EXAMPLES

Example 1

To a 500 mL flask were added 10 g of gatifloxacin and 258 mL of MeOH:H$_2$O, 90:10, mixture. The combination was heated to reflux until a clear solution was obtained. The solution was cooled to ambient temperature in 1 hour and then to 5° C. over 45 minutes. The resulting suspension was then filtered and washed with 120 mL of a MeOH:H$_2$O, 90:10, mixture.

The sample was dried in a vacuum oven at 55° C. for 24 hours. The crystalline form of the sample was analyzed by XRD analysis and found to be form L.

Example 2

To a 250 mL flask were added 10 g of gatifloxacin and 66 mL of absolute ethanol. The mixture was stirred at ambient temperature for 24 hours and then filtered. The filter cake was washed with 20 mL of absolute Ethanol and dried under vacuum for 24 hours. The crystalline form of this sample was analyzed by XRD analysis and showed to be form M.

Example 3

To a 250 mL flask were added 10 g of gatifloxacin and 120 mL of an ethanol-water mixture (EtOH:$H_2O$ 99:1). The combination was heated to reflux until a clear solution was obtained. The mixture was cooled to ambient temperature over 1 hour and then cooled to 5° C. in 1 hour. The resulting suspension was then filtered and washed with 50 mL of a EtOH:$H_2O$, 99:1, mixture.

The crystalline form of this wet cake was analyzed by XRD analysis and found to be form P.

Example 4

To a 250 mL flask were added 10 g of gatifloxacin and 135 mL of a ACN:$H_2O$, 98:2, mixture. The combination was heated to reflux until a clear solution was obtained. The solution was cooled to ambient temperature in 1 hour and then cooled to 5° C. for 1 hour. The resulting suspension was then filtered and washed with 100 ML of an aqueous mixture ACN:$H_2O$ 98:2.

The collected solid was dried in a vacuum oven at 50° C. for 12 hours. The crystalline form of this sample was analyzed by XRD analysis and showed to be form Q.

Example 5

12.67 g of wet gatifloxacin obtained by crystallization from ACN was slurried in 83.6 mL of ethanol for a total slurry time of about 24 hours. Samples of the slurry were taken at slurry times of 2, 4, 6, 8 and 24 hours. The solid was isolated from the slurry by filtration and analyzed by XRD analysis.

The wet isolated solid was found to be form S by XRD analysis.

After drying, the sample was found to be form T2RP.

Example 6

14.93 g of dry material obtained from recrystallization from ACN was slurried in 98.5 mL of ethanol for a total slurry time of 24 hours. Samples of the slurry were taken at 2, 4, 6, 8 and 24 hours. The solid was isolated from the slurry by filtration and analyzed by XRD analysis.

The wet material was found to be form S by XRD analysis.

After drying, the sample was found to be form T2RP.

Example 7 (form J)

3 g of gatifloxacin were slurried in 20 mL of technical IPA. The mixture was stirred at ambient temperature for a slurry time of 24 hours with a magnetic stirrer. Then the mixture was filtered (suction) and the isolated solid rinsed with technical IPA (10 mL). The sample was divided in two portions. The first portion was dried in a vacuum oven at 50° C. for 24 hours and the second portion was dried in an atmospheric oven at 60° C. for 24 hours. These two dried samples were analyzed by XRD analysis and shown to be form J.

Example 8

Dry gatifloxacin (7 g), obtained by crystallization of gatifloxacin from acetonitrile was slurried in absolute ethanol (46.2 mL). The slurry was stirred at ambient temperature for 90 minutes and then filtered (suction). The solid isolated was the dried under vacuum overnight. The material was analyzed by XRD and found to be form T1.

What is claimed is:

1. A crystalline form of gatifloxacin characterized by an x-ray diffraction diagram consisting essentially of a major reflection at about 17.2°±0.2° 2θ.

2. The crystalline form of gatifloxacin of claim 1 having an x-ray diffraction diagram as shown in FIG. 1.

3. A method of making the crystalline gatifloxacin of claim 1 comprising the steps of:
   a) providing, at a temperature of at least about 70° C., a solution of gatifloxacin in a solvent consisting essentially of a mixture of methanol and water, wherein the water is present in the mixture in an amount of about 5 vol-% to about 15 vol-% relative to the methanol,
   b) cooling the solution to obtain a suspension,
   c) isolating a solid from the suspension, and
   d) drying the isolated solid at a temperature of about 40° C. to about 70° C. to obtain the crystalline form of gatifloxacin.

4. The method of claim 3 wherein the solution is cooled to ambient temperature and thereafter to a temperature of about 0° C. to about 10° C.

5. The method of claim 3 wherein the water is present in the mixture in an amount of about 10 vol-% relative to the methanol.

6. The method of claim 3 wherein the isolated solid is dried at a temperature of about 55° C.

7. A crystalline form of gatifloxacin characterized by an x-ray diffraction diagram having reflections at about 8.8°, 14.1°, 17.6°, 18.2°, 22.0°, and 22.6°±0.2° 2θ.

8. The crystalline form of gatifloxacin of claim 7 having an x-ray diffraction diagram as shown in FIG. 2.

9. A method of making the crystalline form of gatifloxacin of claim 8, comprising the steps of:
   a) slurrying gatifloxacin in ethanol, wherein the gatifloxacin slurried is selected from
      i) a crystalline form of gatifloxacin characterized by an x-ray diffraction diagram having reflections at about 12.5°, 20.0°, 20.9°, 22.2°, 24.5°, 25.1°, and 28.0°±0.2° 2θ,
      ii) a crystalline form of gatifloxacin characterized by an x-ray diffraction diagram having reflections at about 7.4°, 8.9°, 9.6°, 11.4°, 12.2°, 12.9°, 14.1°, 16.7°, 21.2°, 21.8°, 24.1°, and 26.0°±0.2° 2θ, and
      iii) mixtures of i) and ii),
   b) isolating a solid from the slurry, and
   c) drying the isolated solid at ambient temperature and pressure to obtain the crystalline form of gatifloxacin of claim 8.

10. A crystalline form of gatifloxacin characterized by an x-ray diffraction diagram having reflections at about 11.1°, 11.7°, 12.5° and 23.0°±0.2° θ.

11. The crystalline form of gatifloxacin of claim 10 having an x-ray diffraction diagram as shown in FIG. 3.

12. A method of making the crystalline form of gatifloxacin of claim 10 comprising the steps of:
   a) providing, at a temperature of at least about 75° C., a solution of gatifloxacin in a solvent consisting essentially of a mixture of ethanol and water, wherein the ethanol is present in the mixture in an amount of at least about 95 vol-% relative to the water,
   b) cooling the solution to obtain a suspension, and
   c) isolating the crystalline form of gatifloxacin from the suspension.

13. The method of claim 12 wherein the solution is cooled to ambient temperature and thereafter to a temperature of about 0° C. to about 10° C.

14. The method of claim 12 wherein the water is present in the mixture in an amount of about 1 vol-% relative to the ethanol.

15. A crystalline form of gatifloxacin characterized by an x-ray diffraction diagram having reflections at about 6.8°, 7.1°, 11.1°, 15.5°, and 17.4°±0.2° 2θ.

16. The crystalline form of gatifloxacin of claim 15 having an x-ray diffraction diagram as shown in FIG. 4.

17. A method of making the crystalline form of gatifloxacin of claim 15 comprising the steps of:
   a) providing, at reflux, a solution of gatifloxacin in a solvent consisting essentially of a mixture of acetonitrile and water, wherein the water is present in the mixture in an amount of about 2 vol-% relative to the acetonitrile,
   b) cooling the solution to obtain a suspension,
   c) isolating a solid from the suspension, and
   d) drying the isolated solid at about 50° C. and a pressure of about 10 to about 400 mm Hg to obtain the crystalline form of gatifloxacin.

18. The method of claim 17, wherein the solution is cooled to ambient temperature and thereafter to a temperature of about 0° C. to about 10° C.

19. A crystalline form of gatifloxacin characterized by an x-ray diffraction diagram having reflections at about 9.3°, 11.0°, 12.0°, 14.5°, 18.6° and 21.2°±0.2° 2θ.

20. The crystalline form of gatifloxacin of claim 19, having an x-ray diffraction diagram as shown in FIG. 5.

21. A method of making the crystalline form of gatifloxacin of claim 19 comprising the steps of:
   a) crystallizing gatifloxacin from acetonitrile,
   b) isolating the crystalline gatifloxacin,
   c) slurrying the isolated crystalline gatifloxacin in a lower alkanol having 1 to 4 carbon atoms for at least about 2 hours, and
   d) isolating the crystalline form of gatifloxacin of claim 19 from the slurry.

22. The method of claim 21 wherein the lower alkanol is ethanol.

23. A crystalline form of gatifloxacin characterized by an x-ray diffraction diagram having reflections at about 7.4°, 8.9°, 9.6°, 11.4°, 12.2°, 12.9°, 14.1°, 16.7°, 21.2°, 21.8°, 24.1°, and 26.0°±0.2° 2θ.

24. The crystalline form of gatifloxacin of claim 23 having an x-ray diffraction diagram as shown in FIG. 6.

25. A method of making the crystalline form of gatifloxacin of claim 23 comprising the steps of:
   a) crystallizing gatifloxacin from acetonitrile,
   b) isolating the crystalline gatifloxacin,
   c) slurrying the isolated crystalline gatifloxacin in ethanol for less than about 2 hours, and
   d) isolating the crystalline form of gatifloxacin of claim 23 from the slurry.

26. A method of making gatifloxacin sesquihydrate comprising the step of maintaining a crystalline form of gatifloxacin characterized by an x-ray diffraction diagram having reflections at about 11.1°, 11.7°, 12.5° and 23.0°±0.2° 2θ at ambient temperature for a time sufficient to effect conversion to the sesquihydrate.

27. The method of claim 26 wherein the crystalline form of gatifloxacin is maintained for about one month.

28. A method of making a crystalline form of gatifloxacin characterized by an x-ray diffraction diagram having reflections at about 13.5°, 19.6°, 20.4°, 23.6°, 25.8°, and 28.5°±0.2° 2θ comprising the step of drying gatifloxacin form K at about 50° C. and a pressure of about 10 mm Hg.

29. The method of claim 28 wherein the gatifloxacin form K is dried for about 24 hours.

30. A method of making a crystalline form of gatifloxacin characterized by an x-ray diffraction diagram having reflections at about 6.7°, 11.3°, 13.8°, and 16.4°±0.2° 2θ comprising the step of drying gatifloxacin form K at about 50° C. and atmospheric pressure.

31. The method of claim 30 wherein the gatifloxacin form K is dried for about 12 to about 18 hours.

32. A method of making a crystalline form of gatifloxacin characterized by an x-ray diffraction diagram having reflections at about 13.5°, 19.6°, 20.4°, 23.6°, 25.8°, and 28.5°±0.2° 2θ comprising the step of maintaining a crystalline form of gatifloxacin characterized by an x-ray diffraction diagram consisting essentially of a major reflection at about 17.2°±0.2° 2θ at ambient temperature for a time sufficient to effect conversion to the crystalline form of gatifloxacin characterized by an x-ray diffraction diagram having reflections at about 13.5°, 19.6°, 20.4°, 23.6°, 25.8°, and 28.5°±0.2° 2θ.

33. The method of claim 32 wherein the crystalline form of gatifloxacin characterized by an x-ray diffraction diagram consisting essentially of a major reflection at about 17.2°±0.2° 2θ is maintained for about 2 months.

34. A method of making gatifloxacin hemihydrate comprising the step of maintaining a crystalline form of gatifloxacin characterized by an x-ray diffraction diagram having reflections at about 8.8°, 14.1°, 17.6°, 18.2°, 22.0°, and 22.6°±0.2° 2θ at room temperature for a time sufficient to effect conversion to the hemihydrate.

35. A method of making the crystalline form of gatifloxacin of claim 23 comprising the step of heating a crystalline form of gatifloxacin characterized by an x-ray diffraction diagram having reflections at about 11.1°, 11.7°, 12.5° and 23.0°±0.2° 2θ at 50° C.

36. A pharmaceutical composition comprising at least one pharmaceutically acceptable excipient and at least one of
   i) a crystalline form of gatifloxacin characterized by an x-ray diffraction diagram consisting essentially of a major reflection at about 17.2°±0.2° 2θ,
   ii) a crystalline form of gatifloxacin characterized by an x-ray diffraction diagram having reflections at about 8.8°, 14.1°, 17.6°, 18.2°, 22.0°, and 22.6°±0.2° 2θ,
   iii) a crystalline form of gatifloxacin characterized by an x-ray diffraction diagram having reflections at about 11.1°, 11.7°, 12.5° and 23.0° 2θ,
   iv) a crystalline form of gatifloxacin characterized by an x-ray diffraction diagram having reflections at about 6.8°, 7.1°, 11.1°, 15.5°, and 17.4°±0.2° 2θ,
   v) a crystalline form of gatifloxacin characterized by an x-ray diffraction diagram having reflections at about 9.3°, 11.0°, 12.0°, 14.5°, 18.6° and 21.2°±0.2° 2θ, or
   vi) a crystalline form of gatifloxacin characterized by an x-ray diffraction diagram having reflections at about 7.4°, 8.9°, 9.6° 11.4°, 12.2°, 12.9°, 14.1°, 16.7°, 21.2°, 21.8°, 24.1°, and 26.0°±0.2° 2θ.

* * * * *